United States Patent
Li

(10) Patent No.: US 10,695,164 B2
(45) Date of Patent: Jun. 30, 2020

(54) COVERED ENDOVASCULAR STENT-GRAFT

(71) Applicant: Evans Scientific (Beijing) Co., Ltd, Beijing (CN)

(72) Inventor: Lei Li, Beijing (CN)

(73) Assignee: EVANS SCIENTIFIC (BEIJING) CO., LTD, Beijing (CN)

( * ) Notice: Subject to any disclaimer, the term of this patent is extended or adjusted under 35 U.S.C. 154(b) by 0 days.

(21) Appl. No.: 16/061,587

(22) PCT Filed: Oct. 19, 2016

(86) PCT No.: PCT/CN2016/102623
§ 371 (c)(1),
(2) Date: Jun. 12, 2018

(87) PCT Pub. No.: WO2017/101582
PCT Pub. Date: Jun. 22, 2017

(65) Prior Publication Data
US 2018/0360590 A1 Dec. 20, 2018

(30) Foreign Application Priority Data
Dec. 14, 2015 (CN) .......................... 2015 1 0929040

(51) Int. Cl.
*A61F 2/07* (2013.01)
*A61F 2/82* (2013.01)
*A61L 31/02* (2006.01)
*A61L 31/10* (2006.01)
*B05D 1/04* (2006.01)
*B05D 1/00* (2006.01)

(52) U.S. Cl.
CPC .................. *A61F 2/07* (2013.01); *A61F 2/82* (2013.01); *A61L 31/022* (2013.01); *A61L 31/10* (2013.01); *B05D 1/04* (2013.01); *A61F 2002/072* (2013.01); *A61F 2220/0025* (2013.01); *A61F 2250/0014* (2013.01); *A61L 2420/02* (2013.01); *B05D 1/005* (2013.01)

(58) Field of Classification Search
CPC ....................................................... A61F 2/07
See application file for complete search history.

(56) References Cited

U.S. PATENT DOCUMENTS

| 2004/0199242 A1 | 10/2004 | Hong et al. |
| 2008/0188924 A1 | 8/2008 | Prabhu |
| 2014/0188212 A1* | 7/2014 | Haselby .................. D01D 5/003 623/1.15 |

FOREIGN PATENT DOCUMENTS

| CN | 1715312 A | 1/2006 |
| CN | 101627933 A | 1/2010 |
| CN | 101703812 A | 5/2010 |
| CN | 203436435 U | 2/2014 |
| JP | 2010-528812 A | 8/2010 |

OTHER PUBLICATIONS

Communication from the European Patent Office in counterpart European Application No. 16874640.2, dated Nov. 26, 2018.
Communication from the Japanese Patent Office in counterpart application No. 2018-532293, dated May 14, 2019.

* cited by examiner

Primary Examiner — Matthew W Schall
(74) Attorney, Agent, or Firm — Arent Fox LLP

(57) ABSTRACT

Provided is a covered endovascular stent-graft comprising a first membrana tectoria for modeling a vascular shape and a stent-graft skeleton fitted to the outside of the first membrana tectoria, at least part of the outer surface of the stent-graft skeleton being covered with a second membrana tectoria; the first membrana tectoria and the second membrana tectoria are combined so that at least part of the stent-graft skeleton is covered between the first membrana tectoria and the second membrana tectoria, wherein the first membrana tectoria and/or the second membrana tectoria is/are a polyvinylidene fluoride resin membrana tectoria. The polyvinylidene fluoride resin membrana tectoria of the covered endovascular stent-graft makes the cost reduced and has good mechanical properties and biological properties.

9 Claims, No Drawings

COVERED ENDOVASCULAR STENT-GRAFT

CROSS REFERENCE

This application claims priority to Chinese Patent Application No. 201510929040.9, filed on Dec. 14, 2015, and International Patent Application No. PCT/CN2016/102623, filed on Oct. 19, 2016, both of which are hereby incorporated by reference in their entireties.

TECHNICAL FIELD

The present invention relates to the field of interventional therapy medical instruments, and more particularly relates to a covered endovascular stent-graft.

BACKGROUND ART

The interventional therapy of an endovascular stent-graft is widely used in the therapy of cardiovascular and cerebrovascular diseases such as vascular occlusion. For example, it is often necessary to implant a covered stent-graft in great blood vessels such as aorta and metal stent-grafts in other small blood vessels. The covered stent-graft not only retains the support function of a common covered stent-graft, but also can effectively improve the abnormal hemodynamics of a diseased blood vessel. The current covered stent-graft is generally covered with a membrana tectoria made of polytetrafluoroethylene resin, it is necessary to melt the polytetrafluoroethylene resin at a high temperature, and then the membrana tectoria is bonded to a stent-graft substrate under pressure. Under the action of heat, the middle of the membrana tectoria tends to form a suspension, resulting in non-uniform covering of the membrana tectoria, and the entire process consumes a large amount of energy, which makes the existing covered stent-graft expensive.

SUMMARY OF THE INVENTION

The present invention is directed to a covered endovascular stent-graft, intended to overcome the defect that a conventional polytetrafluoroethylene resin membrana tectoria needs to be treated at a high temperature to result in non-uniform forming of the membrana tectoria.

To this end, the present invention provides a covered endovascular stent-graft including a first membrana tectoria for modeling a vascular shape and a stent-graft skeleton fitted to the outside of the first membrana tectoria, at least part of the outer surface of the stent-graft skeleton being covered with a second membrana tectoria; the first membrana tectoria and the second membrana tectoria are combined so that at least part of the stent-graft skeleton is covered between the first membrana tectoria and the second membrana tectoria, wherein the first membrana tectoria and/or the second membrana tectoria is/are a polyvinylidene fluoride resin membrana tectoria.

Preferably, the thickness of the first membrana tectoria is within a range of 0.01 to 0.1 mm, and the thickness of the second membrana tectoria is within a range of 0.01 to 0.1 mm.

Preferably, the stent-graft skeleton is a metal stent-graft skeleton and/or a polymer stent-graft skeleton.

Preferably, metal in the metal stent-graft skeleton includes stainless steel and/or nickel titanium alloy.

Preferably, the first membrana tectoria and/or the second membrana tectoria is/are obtained by a membrane-forming treatment on a polyvinylidene fluoride resin solution.

Preferably, the weight ratio of polyvinylidene fluoride resin to a solvent in the polyvinylidene fluoride resin solution is 1:(4-100).

Preferably, the polyvinylidene fluoride resin has a melt mass flow rate of 1-20 g/10 min.

Preferably, the solvent is at least one of dimethylformamide, dimethylacetamide, dimethyl sulfoxide, or methyl ethyl ketone.

Preferably, the membrane-forming treatment includes a casting membrane-forming treatment, a controlled deposition membrane-forming treatment, and a spray coating membrane-forming treatment.

Preferably, the spray coating membrane-forming treatment has a temperature of 10-90° C.

Through the above technical scheme, polyvinylidene fluoride resin is dissolved in a solvent such as dimethylformamide to obtain a membrana tectoria, thereby overcoming the defect that a conventional polytetrafluoroethylene resin membrana tectoria needs to be treated at a high temperature to result in non-uniform forming of the membrana tectoria. The operation is simple, and the cost is reduced. The covered endovascular stent-graft of the present invention has good mechanical properties and biological properties.

Additional features and advantages of the present invention will be set forth in part in the following detailed description of the invention.

DETAILED DESCRIPTION OF THE INVENTION

Embodiments of the present invention will be described in detail below. It will be appreciated that the embodiments described herein are only used to illustrate and explain the present invention and are not intended to limit the present invention.

The present invention provides a covered endovascular stent-graft including a first membrana tectoria for modeling a vascular shape and a stent-graft skeleton fitted to the outside of the first membrana tectoria, at least part of the outer surface of the stent-graft skeleton being covered with a second membrana tectoria; the first membrana tectoria and the second membrana tectoria are combined so that at least part of the stent-graft skeleton is covered between the first membrana tectoria and the second membrana tectoria, wherein the first membrana tectoria and/or the second membrana tectoria is/are a polyvinylidene fluoride resin membrana tectoria.

In a preferred embodiment of the present invention, a core may be first designed and processed according to a vascular structure of a stent-graft to be implanted, then a covered stent-graft may be processed on the core, and the core and the covered stent-graft may be separated to obtain the covered endovascular stent-graft of the present invention. In order to accurately and conveniently obtain the core fitting the vascular structure, it is preferable that the core may be processed by a 3D printing technology. Specifically, in the design of a core, a vascular structure of a stent-graft portion to be implanted may be obtained through medical means such as angiography, e.g., CT angiography, then a 3D model fitting the vascular structure is constructed in a computer according to the vascular structure of the stent-graft portion to be implanted, and then the core is processed and manufactured through a 3D printer. It should be noted that since the finally obtained endovascular stent-graft needs to adapt to the inner wall of a blood vessel, while ensuring that the outer surface structure of the core adapts to the inner wall structure of the blood vessel, the dimensions of the core may be designed in accordance with an error precision needed for a doctor, and processing methods for different error precisions should fall within the protection scope of the present invention. That is, since the covered stent-graft is manufactured based on the outer surface of the core, the covered stent-graft needs to be implanted on the inner wall of the blood vessel. Therefore, when processing the core, it is necessary to design the core according to the requirements of the doctor, such that the dimension of the outer surface of the core is smaller than that of the inner wall of the blood vessel because of the needed error, to make the final covered stent-graft adapt to the inner wall of the blood vessel. The core may be a hollow structure or a solid structure, which is not limited by the present invention. In consideration of the convenience of processing, the core is preferably a solid structure. The core is designed and processed according to a human vascular structure of a stent-graft to be implanted. After processing the covered stent-graft on the core, it is necessary to separate the core from the covered stent-graft, thereby obtaining a covered endovascular stent-graft having a cavity structure.

In order to complete the processing of the covered stent-graft, it is necessary to combine the stent-graft skeleton and the membrana tectoria to each other on the core. In order to facilitate the foregoing combination, a first membrana tectoria is first processed on the core, then the stent-graft skeleton is fitted to the core processed with the first membrana tectoria, and a second membrana tectoria is processed on the stent-graft skeleton, so that the first membrana tectoria and the second membrana tectoria are combined to achieve the combination of the membrana tectoria material and the stent-graft skeleton. That is, the stent-graft skeleton is firmly sandwiched between a front membrana tectoria and a rear membrana tectoria to achieve a stable combination thereof.

In order to facilitate the processing of the core, a dissolvable material may be used to process the core, for example, a water-soluble material may be used to process the core. More specifically, the core may be processed using a saccharide material, so that a solid core can be easily dissolved. Preferably, the saccharide material may include at least one of monosaccharide, disaccharide, or water-soluble polysaccharide. In addition, it is important to use a liquid-soluble material to process the core in order to better separate the core from the finished covered stent-graft. Preferably, in order to quickly separate the core from the covered stent-graft, the core may be removed using liquid capable of dissolving the core, so that the core is separated from the covered stent-graft. In other embodiments, the core may also be made of a meltable material, as long as the core is melted using a heating device when separating the core. Such a deformation mode should also fall within the protection scope of the present invention.

According to the present invention, the first membrana tectoria and/or the second membrana tectoria is/are a polyvinylidene fluoride resin membrana tectoria. If the polyvinylidene fluoride resin membrana tectoria is too thin, the strength of the membrana tectoria may be reduced, and thus the membrana tectoria may be easily broken. In the present invention, the thickness of the first membrana tectoria is preferably within a range of 0.01 to 0.1 mm, and the thickness of the second membrana tectoria is preferably within a range of 0.01 to 0.1 mm.

According to the present invention, the stent-graft skeleton may be selected from conventional skeleton materials in the art, and may be, for example, a metal stent-graft skeleton and/or a polymer stent-graft skeleton. Metal in the metal stent-graft skeleton may include stainless steel and/or nickel titanium alloy. The stent-graft skeleton may be a single-circle ring, and different sizes of stent-graft rings are selected according to the specification of the core, for being combined with the membrana tectoria after fitted to the core. In addition, the stent-graft skeleton may also be an entire thread, which is fitted to the outer surface of the core by winding and covering, so as to obtain an appropriate stent-graft skeleton.

According to the present invention, the first membrana tectoria and/or the second membrana tectoria is/are obtained by a membrane-forming treatment on a polyvinylidene fluoride resin solution. The weight ratio of polyvinylidene fluoride resin to a solvent in the polyvinylidene fluoride resin solution may play a role in dissolving the polyvinylidene fluoride resin within a wider range. For example, the weight ratio of the polyvinylidene fluoride resin to the solvent may be 1:(4-100).

According to the present invention, the polyvinylidene fluoride (PVDF) resin mainly refers to a vinylidene fluoride homopolymer or a copolymer of vinylidene fluoride and other small amounts of a fluorine-containing vinyl monomer. For the same type of high polymers, the molecular weight may be compared through the melt mass flow rate (MFR). The higher the degree of polymerization is, the larger the molecular weight is, and the smaller the melt mass flow rate is. Otherwise, the smaller the molecular weight is, the larger the melt mass flow rate is. In the present invention, the polyvinylidene fluoride resin may have a melt mass flow rate of 1-20 g/10 min.

The solubility of the polyvinylidene fluoride resin in the solvent varies with different polymerization processes and formulae of the polyvinylidene fluoride resin. Conventional solvents include acetone, tetrahydrofuran, methyl ethyl ketone, dimethylformamide, dimethylacetamide, tetramethyl urea, dimethyl sulfoxide, trimethyl phosphate, N-methyl pyrrolidone, butyrolactone, isophorone, carbitol acetate, methyl isobutyl ketone, butyl acetate, cyclohexanone, diisobutyl ketone, ethyl acetoacetate, and triethyl phosphate. According to the present invention, the solvent is at least one of dimethylformamide, dimethylacetamide, dimethyl sulfoxide, or methyl ethyl ketone.

According to the present invention, the membrane-forming treatment may be performed using a common polymer membrane-forming treatment method in the art such as casting, electrospinning, controlled deposition or spray coating The casting refers to a method of uniformly casting a polymer solution on a dry, smooth and clean substrate and then drying in a constant temperature oven to form a membrane. The electrospinning refers to: generating a charged jet flow by subjecting the polymer solution to surface tension under a high-voltage electrostatic field, and refining and splitting the jet flow to make finally-cured high-polymer fibers fall on the substrate to form a fiber membrane. The controlled deposition refers to a method of depositing a membrane-forming material on a carrier and controlling conditions to form a membrane. The spray coating refers to: using an air pressure spray gun to atomize a solution using high pressure air, pushing a droplet to a substrate under load gas, and depositing and drying to form a membrane. When the membrane-forming treatment is performed using spray coating, the core may be sprayed to form a membrana tectoria at a lower temperature. Preferably, the spray coating membrane-forming treatment has a temperature of 10-90° C.

The following further illustrates the present invention with embodiments, but does not limit the present invention.

Embodiment 1

A vascular structure of a stent-graft portion to be implanted was obtained through CT angiography, then a 3D model fitting the vascular structure was constructed in a computer according to the vascular structure of the stent-graft portion to be implanted, and then a core was processed and manufactured through a 3D printer. The core was obtained by mixing maltose, sucrose and fructose in a mass ratio of 1:1:1.

Polyvinylidene fluoride resin FR901 (purchased from Shanghai 3F, and having a melt mass flow rate of 16 g/10 min) and dimethylformamide were mixed in a weight ratio of 1:10, and after stirring for 4 hours, they were left to stand for defoaming to obtain a polyvinylidene fluoride resin solution.

When an air pressure spray gun was used at a pressure of 0.3 MPa and at a temperature of 30° C. and the distance between a nozzle and the surface of the core was 150 mm, the obtained polyvinylidene fluoride resin solution was sprayed onto the surface of the core to form a continuous first stent-graft membrana tectoria with a thickness of 0.05 mm.

A stainless steel stent-graft skeleton was fitted to the core sprayed with the first stent-graft membrana tectoria, then the polyvinylidene fluoride resin solution was sprayed again using the air pressure spray gun along the surface of the stainless steel stent-graft skeleton under the same working conditions to form a non-continuous second stent-graft membrana tectoria having a thickness of 0.05 mm, the second stent-graft membrana tectoria was combined with the first stent-graft membrana tectoria, and the stainless steel stent-graft skeleton was covered therein.

The core was dissolved in water to obtain the covered endovascular stent-graft of the present invention.

The obtained covered stent-graft was implanted into the aorta of an experimental animal (rabbit). Angiography was performed 4 weeks, 12 weeks and 24 weeks later to observe the patency of the covered stent-graft implanted into a blood vessel, the stent-graft attachment performance, the presence or absence of migration, etc.

Animal implantation experiments showed that all experimental animals (rabbits) survived well during the follow-up period, and the blood vessels in the stent-graft implantation site remained unobstructed, and no thrombus formation was observed. The covered stent-graft was free of shrinkage, rupture, complications, blood leakage, and stent-graft migration, and had a better covered stent-graft attachment performance and good biocompatibility.

Embodiment 2

A vascular structure of a stent-graft portion to be implanted was obtained through CT angiography, then a 3D model fitting the vascular structure was constructed in a computer according to the vascular structure of the stent-graft portion to be implanted, and then a core was processed and manufactured through a 3D printer. The core was obtained by mixing maltose, sucrose and fructose in a mass ratio of 1:2:5.

Polyvinylidene fluoride resin FR921 (purchased from Shanghai 3F, and having a melt mass flow rate of 2 g/10 min) and dimethylformamide were mixed in a weight ratio of 1:80, and after stirring for 4 hours, they were left to stand for defoaming to obtain a polyvinylidene fluoride resin solution.

The obtained polyvinylidene fluoride resin solution was poured into a mold in which the core was placed, and the polyvinylidene fluoride resin solution was cast on the surface of the core to form a continuous first stent-graft membrana tectoria having a thickness of 0.1 mm.

A nickel titanium alloy stent-graft skeleton was fitted to the cast core covered with the first stent-graft membrana tectoria, and then placed again in the mold, so that the polyvinylidene fluoride resin solution was cast again to form a second stent-graft membrana tectoria having a thickness of 0.1 mm, the second stent-graft membrana tectoria was combined with the first stent-graft membrana tectoria, and the nickel titanium alloy stent-graft skeleton was covered therein.

The core was dissolved in water to obtain the covered endovascular stent-graft of the present invention.

The obtained covered stent-graft was implanted into the aorta of an experimental animal (rabbit). Angiography was performed 4 weeks, 12 weeks and 24 weeks later to observe the patency of the covered stent-graft implanted into a blood vessel, the stent-graft attachment performance, the presence or absence of migration, etc.

Animal implantation experiments showed that all experimental animals (rabbits) survived well during the follow-up period, and the blood vessels in the stent-graft implantation site remained unobstructed, and no thrombus formation was observed. The covered stent-graft was free of shrinkage, rupture, complications, blood leakage, and stent-graft migration, and had a better covered stent-graft attachment performance and good biocompatibility.

What is claimed is:

1. A covered endovascular stent-graft, which is characterized by comprising a first membrana tectoria for modeling a vascular shape and a stent-graft skeleton fitted to an outside of the first membrana tectoria, at least part of the outer surface of the stent-graft skeleton being covered with a second membrana tectoria; the first membrana tectoria and the second membrana tectoria being combined so that at least part of the stent-graft skeleton is covered between the first membrana tectoria and the second membrana tectoria, wherein the first membrana tectoria or the second membrana tectoria is a polyvinylidene fluoride resin membrana tectoria, wherein the polyvinylidene fluoride resin has a melt mass flow rate of 1-20g/10min, and wherein the stent-graft skeleton and the first membrana tectoria or the second membrana tectoria are combined with each other on a core comprising a dissolvable material to facilitate processing of the core.

2. The covered endovascular stent-graft according to claim 1, wherein a thickness of the first membrana tectoria is within a range of 0.01 to 0.1 mm, and a thickness of the second membrana tectoria is within a range of 0.01 to 0.1 mm.

3. The covered endovascular stent-graft according to claim 1, wherein the stent-graft skeleton is a metal stent-graft skeleton or a polymer stent-graft skeleton.

4. The covered endovascular stent-graft according to claim 3, wherein metal in the metal stent-graft skeleton comprises stainless steel or nickel titanium alloy.

5. The covered endovascular stent-graft according to claim 1, wherein the first membrana tectoria or the second membrana tectoria is obtained by a membrane-forming treatment on a polyvinylidene fluoride resin solution.

6. The covered endovascular stent-graft according to claim 5, wherein a weight ratio of polyvinylidene fluoride resin to a solvent in the polyvinylidene fluoride resin solution is 1: (4-100).

7. The covered endovascular stent-graft according to claim 6, wherein the solvent is at least one of dimethylformamide, dimethylacetamide, dimethyl sulfoxide, or methyl ethyl ketone.

8. The covered endovascular stent-graft according to claim 5, wherein the membrane-forming treatment comprises a casting membrane-forming treatment, a controlled deposition membrane-forming treatment, and a spray coating membrane-forming treatment.

9. The covered endovascular stent-graft according to claim 8, wherein the spray coating membrane-forming treatment has a temperature of 10-90° C.

\* \* \* \* \*